United States Patent [19]

Collins et al.

[11] Patent Number: 4,745,809

[45] Date of Patent: May 24, 1988

[54] COMPOSITE ANALYZER TESTER

[75] Inventors: Richard M. Collins, East Setauket; Richard F. Chance, Bayport, both of N.Y.

[73] Assignee: Grumman Aerospace Corporation, Bethpage, N.Y.

[21] Appl. No.: 895,789

[22] Filed: Aug. 12, 1986

[51] Int. Cl.$^4$ ............................................. G01N 29/04
[52] U.S. Cl. ...................................... 73/661; 73/601; 73/597
[58] Field of Search ................. 73/661, 643, 629, 597, 73/570, DIG. 1, 601

[56] References Cited

U.S. PATENT DOCUMENTS

| | | | |
|---|---|---|---|
| 3,403,547 | 10/1968 | Schwartz | 73/661 |
| 4,196,629 | 4/1980 | Philips | 73/661 |
| 4,307,611 | 12/1981 | Opara | 73/629 |
| 4,523,473 | 6/1985 | Chamuel | 73/643 |
| 4,527,419 | 7/1985 | Dimeff et al. | 73/661 |

*Primary Examiner*—Anthony V. Ciarlante
*Attorney, Agent, or Firm*—Scully, Scott Murphy and Presser

[57] ABSTRACT

A single composite analyzer tester instrument capable of nondestructively analyzing and testing several different properties of graphite-resin materials, such as the thickness, sonic velocity, relative sonic amplitude and relative electrical conductivity thereof. The instrument incorporates therein a magnetic induction circuit for measuring the thickness of the test material, which includes a magnetic induction probe with a magnetic induction coil which is placed adjacent to the outer surface of the material. The instrument also includes an ultrasonic pulse-echo circuit for performing two separate but related tests, a measurement of the ultrasonic velocity of the test material, and also a measurement of the relative change in amplitude of an ultrasonic pulse as it traverses the test material from an outer surface thereof to an inner surface, where it is echoed back to the outer surface for detection. This circuit includes an acoustic probe which is placed adjacent to the outer surface of the test material, at the same location where the first probe was placed. Finally, the instrument incorporates therein an eddy current circuit for measuring the relative electrical conductivity of the test material. This circuit includes an eddy current probe with an eddy current coil which is placed adjacent to the outer surface of the test material at the same location as the two previous probes. The magnetic induction circuit, the utlrasonic pulse-echo circuit, and the eddy current circuit are all implemented in a single microprocessor-based unit utilizing extensive digital signal processing. Moreover, the magnetic induction probe, the acoustic probe, and the eddy current probe are each attached to, and detachable from, the console of the unit by electrical plug connections.

9 Claims, 2 Drawing Sheets

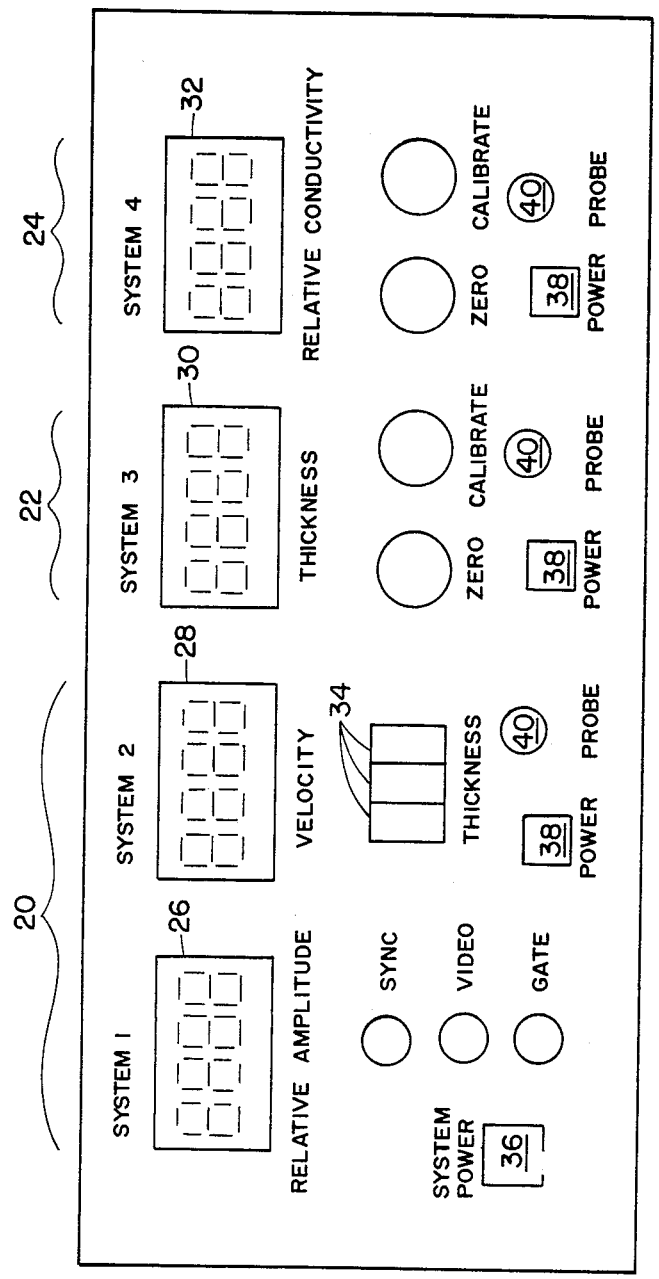
FIG.2 - FRONT PANEL SKETCH OF CAT

COMPOSITE ANALYZER TESTER

BACKGROUND OF THE INVENTION

1. Field of the Invention

The present invention relates generally to a composite analyzer tester for nondestructively testing and analyzing materials, and more particularly pertains to a composite analyzer tester for nondestructively analyzing the physical properties and gaging the thickness of advanced graphite-resin composite materials. Such graphite-resin composite materials are being utilized with a greater frequency of application in the construction of airplane components, such as for the aircraft skin and in other substructural components thereof.

2. Discussion of the Prior Art

The nondestructive testing of advanced fiber-matrix materials, such as graphite-resin composite materials and components, has been developed to provide a high level of assurance of the quality and structural integrity of such materials and components. The individual fiber and matrix material components that make up such a composite are often of non-uniform quality and moreover are laminated in different and varied patterns. Additionally, fabricators can be expected to make occasional human errors in the number and spacing of plies in the layup. Slight changes in curing cycles and rates of heating can also have major effects on mechanical properties, but no obvious effect on the visual appearance of the finished parts. In general, the deviation in properties for composite materials on multiple tests is far greater than considered acceptable for established metal technology. Refined and improved nondestructive testing apparatus and methods must be developed to allow inspection to establish, with greater assurance, the exact quality of the part under surveillance.

Many individual inspection, testing and analysis techniques have been developed for such fiber-matrix ultrasonic testing, magnetic induction testing, electrical conductivity testing, testing by liquid penetrants, thermal infrared testing, and by visual inspections thereof.

SUMMARY OF THE INVENTION

Accordingly, it is a primary object of the present invention to provide a single composite analyzer tester instrument capable of nondestructively analyzing and testing several different properties of fiber-matrix materials such as graphite-resin materials. A further object of the subject invention is the provision of a composite-analyzer tester instrument as described for testing several different properties of graphite-resin materials such as the thickness, sonic velocity, relative sonic amplitude and relative electrical conductivity thereof.

In accordance with the teachings herein, the present invention provides a composite analyzer tester for nondestuctively testing and analyzing the physical properties and gaging the thickness of a test material, such as an advanced graphite-resin composite material. The instrument incorporates therein a magnetic induction circuit for measuring the thickness of the test material, which includes a magnetic induction probe with a magnetic induction coil which is placed adjacent to the outer surface of the material. The magnetic induction coil is energized at a relatively low frequency below one magahertz, and the resultant impedance of the coil in the magnetic induction circuit is a measurement of the thickness of the test material. The magnetic induction circuit is capable of providing nondestructive process control such as in measuring the thickness of uncured fiber-resin material, the thickness of a partially cured (B-staged) fiber-resin laminate, and the thickness of a cured laminated structure. The instrument also included an ultrasonic pulse-echo circuit for performing two separate but related tests, a measurement of the ultrasonic velocity of the test material, and also a measurement of the relative change in amplitude of an ultrasonic pulse as it traverses the test material from an outer surface thereof to an inner surface, where it is echoed back to the outer surface for detection. This circuit includes an acoustic probe which is placed adjacent to the outer surface of the test material, at the same location where the first probe was placed. The acoustic probe generates an ultrasonic pulse which is introduced into the test material, and then detects the echoed ultrasonic pulse. Finally, the instrument incorporates therein an eddy current circuit for measuring the relative electrical conductivity of the test material. This circuit includes an eddy current probe with an eddy current coil which is placed adjacent to the outer surface of the test material at the same location as the two previous probes. The eddy current coil is then energized at a relatively high frequency above one megahertz to generate an alternating magnetic field in and around the coil. This alternating magnetic field induces an alternating electric field in the test material which has eddy currents and an alternating magnetic field associated therewith. This associated magnetic field in turn affects the alternating magnetic field of the eddy current coil, such that the resultant impedance of the eddy current coil in the eddy current circuit provides a measurement of the electrical conductivity of the test material.

In greater detail, the magnetic induction circuit, the ultrasonic pulse-echo circuit, and the eddy current circuit are all implemented in a single microprocessor-based unit utilizing extensive digital signal processing. Moreover, the magnetic induction probe, the acoustic probe, and the eddy current probe are each attached to, and detachable from, the console of the unit by electrical plug connections.

The first measurement taken is of the thickness of the material, as this measurement is used later by the pulse-echo circuit in its determination of the ultrasonic velocity through the material. The thickness of the material is measured by the magnetic induction circuit, and while using this circuit, an element of uniform magnetic permeability is placed in close contact with the inner surface of the test material, opposite the placement of the magnetic induction probe on the outer surface thereof, to complete a magnetic circuit with the magnetic induction coil, with the test material being located therebetween. The magnetic induction circuit then energized the magnetic induction coil at a relatively low frequency of approximately fifty kilohertz. In this arrangement, the test material essentially acts as a spacer between the coil and the element, and the distance therebetween determines the impedance of the magnetic circuit, such that a measurement thereof is also representative of the thickness of the test material.

The measured thickness is then utilized by the pulse-echo circuit in its measurement of the ultrasonic velocity in the material. The measured thickness can be entered automatically through the microprocessor, or manually as in one illustrated embodiment. The acoustic probe preferable comprises a piezoelectric transducer which is initially pulsed to produce an ultrasonic pulse, and which is then monitored for detection of the echoed ultrasonic pulse. The ultrasonic pulse circuit preferable energized the piezoelectric transducer with pulses at a frequency of approximately five megahertz. The pulse-echo circuit takes two separate measurements, the acoustic or sonic velocity through the test material, and also the attenuation of each pulse traversing the test material to its opposite surface and being refelected therefrom as an echo back to the probe.

The last measurement is by the eddy current circuit, and for this measurement the eddy current probe is placed at the same location as the previous two probes. The eddy current circuit then energizes the eddY current coil at a frequency of above one megahertz, typically around five megahertz, and the impedance of the eddy current coil in the circuit provides a measurement of the elctrical conductivity of the test material.

BRIEF DESCRIPTION OF THE DRAWINGS

The foregoing objects and advantages of the present invention for a composite analyzer tester may be more readily understood by one skilled in the art with reference being had to the following detailed description of several preferred embodiments thereof, taken in conjunction with the accompanying drawings wherein like elements are designated by identical reference numerals throughout the several views, and in which:

FIG. 2 illustrates a front elevational view of the front panel of a second, slightly different embodiment of a composite analyzer tester pursuant to the teachings herein.

DETAILED DESCRIPTION OF THE DRAWINGS

Figure 1:
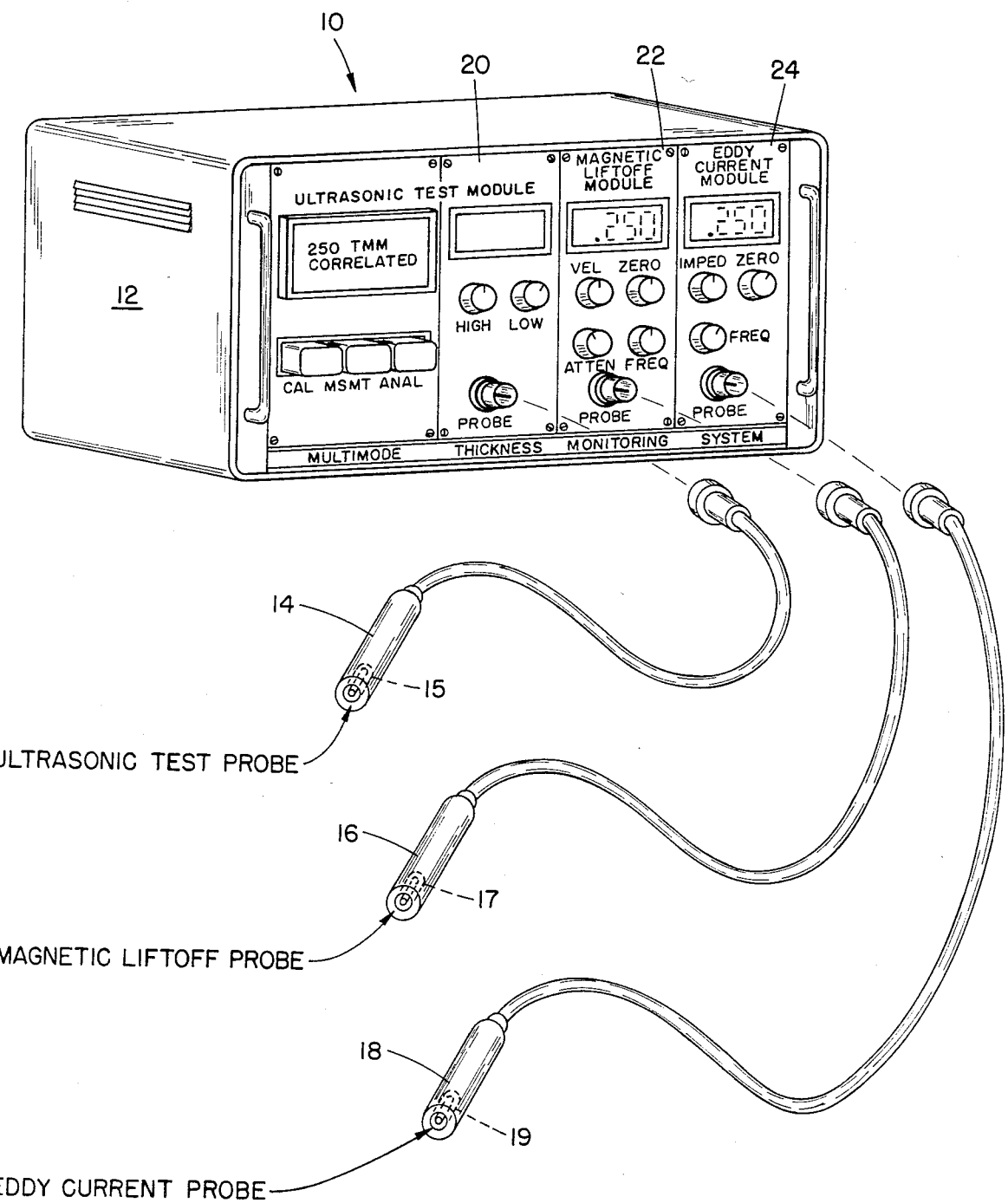
FIG. 1 is a front perspective view of a first exemplary embodiment of a composite analyzer tester instrument constructed pursuant to the teachings of the present invention, and illustrates also the three different probes utilized in the several tests and measurements performed by the instrument.

Referring to the drawings in detail, FIG. 1 illustrates a first embodiment of a Composite Analyzer Tester (CAT) instrument 10 for nondestructively analyzing the physical properties and gaging the thickness of advanced graphite-resin composites. The CAT instrument 10 is capable of performing four various modes of ultrasonic, magnetic, and electrical (eddy current) tests, on a graphite-resin composite, and is integrated into one convenient, protable cabinet 12. All testing is conducted by consecutively placing probes 14, 16, and 18 on a particular surface location of the material.

The CAT instrument 10 consists of four systems of analysis/gaging circuitry:

System 1: RELATIVE AMPLITUDE—A microprocessor-based ultrasonic pulse-echo circuit module 20 measures the change in the amplitude of an ultrasonic pulse making a round trip (reflected as an echo) through the material. This measurement is made with the probe 14.

System 2: VELOCITY—The microprocessor-based ultrasonic pulse-echo circuit module 20 simultaneously measures the ultrasonic velocity of the material (and also uses the probe 14) while System 1 is measuring the echo relative amplitude.

System 3: THICKNESS—A low frequency, microprocessor-based, magnetoinduction circuit module 22 measures the mechanical thickness of the graphite composite, without reacting to the properties or variation in the properties of the composite. A ferromagnetic sheet of uniform magnetic permeability is placed in firm and intimate contact with the opposite surface of the composite in order to make this measurement. This measurement is made with the probe 16.

System 4: CONDUCTIVITY—A high frequency, microprocessor-based eddy current circuit module 24 is designed to measure the relative electrical conductivity or relative electrical conductance of the graphite composite. The test frequency and and eddy current probe 18 are designed to minimize "thickness effects" at the thinner end of the expected thickness range for the composites.

The magnetic induction probe 16 includes a magnetic induction coil 17 which is placed adjacent to the outer surface of the test material such that the central longitudinal axis of the coil is generally perpendicular to the surface of the material. While using this circuit, an element of uniform magnetic permeability is placed in close contact with the inner surface of the test material, opposite the placement of the magnetic induction probe 16 on the outer surface thereof, to complete a magnetic circuit with the magnetic induction coil 17, with the test material being located therebetween. The magnetic induction circuit then energizes the magnetic induction coil at a relatively low frequency of approximately fifty kilohertz. In this arrangement, the test material essentially acts as a spacer between the coil and the element, and the distance therebetween determines the impedance of the magnetic circuit, such that a measurement thereof is also representative of the thickness of the test material.

The measured thickness is then utilized by the Pulse-echo circuit in its measurement of the ultrasonic velocity in the material, and can be entered therein automatically through the microprocessor or manually. The acoustic probe 14 preferably comprises a piezoelectric transducer 15 which is initially pulsed to produce an ultrasonic pulse, and which is then monitored for detection of the echoed ultrasonic pulse. The ultrasonic pulse circuit preferably energizes the piezoelectric transducer with pulses at a frequency of approximately five megahertz. The pulse-echo circuit takes two separate measurements, the acoustic or sonic velocity through the test material, and also the attenuation of each pulse traversing the test material to its opposite surface and being reflected therefrom as an echo back to the probe.

The last measurement is by the eddy current circuit, and for this measurement the eddy current probe 18 is placed at the same location as the previous two probes. The eddy current probe 18 includes an eddy current coil 19 which is placed adjacent to the outer surface of the test material such that the central longitudinal axis of the coil is generally perpendicular to the surface of the material. The coil is then energized at a relatively high frequency above one megahertz, typically around five megahertz, to generate an alternating magnetic field which induces an alternating electric field in the test material having eddy currents and an alternating magnetic field associated therewith, with the associated magnetic field associated therewith, with the associated magnetic field affecting the alternating magnetic field of the eddy current coil, such that the resultant impedance of the eddy current coil in the eddy current circuit provides a measurement of the electrical conductivity of the test material.

FIG. 2 illustrates a slightly modified arrangement of a front panel of a CAT instrument, having a System 1 display 26, a System 2 display 28, a System 3 display 30, a System 4 display 32, thumbnail entry switches 34 for manual entry of the thickness reading on display 30 into the System 2 velocity measuring circuit, an overall system power switch 36, individual system power switches 38, probe jacks 40, and instrument adjustment setting for zero, calibrate, sync, video, and gate.

During operation of the embodiment of FIG. 2, the mechanical thickness of the graphite-resin composite is first gaged with the magnetic induction system 22 using the probe 16. The resultant digital value then on the System 3 display 30 is entered into the ultrasonic test module 20 by thumbwheel switches 34—programmed into the thickness entry digital switch of the ultrasonic VELOCITY System. The probe 14 for the VELOCITY System is then placed at the identical location where the mechanical thickness was gaged, and the relative ultrasonic amplitude and ultrasonic velocity values are digitally displayed on the respective system readouts 26, 28. The relative electrical property (conductivity/conductance) is then measured by placing the probe 18 at the same location as the three previous measurements. Thus, all four measurements (thickness, velocity, relative amplitude and relative conductivity) can be made quickly with the CAT instrument of the present invention.

While several embodiments and variations of the present invention for a composite analyzer tester are described in detail herein, it should be apparent that the disclosure and teachings of the present invention will suggest many alternative designs to those skilled in the art.

What is claimed is:

1. A composite analyzer tester for nondestructively testing and analyzing the physical properties and gaging the thickness of a test material, comprising:
   a. a magnetic induction circuit for measuring the thickness of the material, which includes a magnetic induction probe having a magnetic induction coil which is placed adjacent to the outer surface of the material and is energized at a relatively low frequency below one megahertz, and wherein the resultant impedance of the in the magnetic induction circuit is a measurement of the thickness of the test material;
   b. an ultrasonic pulse-echo circuit for measuring the ultrasonic velocity of the test material in which said measurement of the thickness of the test material is utilized, and for also measuring the relative change in amplitude of an ultrasonic pulse transversing the test material from an outer surface thereof to an inner surface, whereat it is echoed back to the outer surface for detection, including an acoustic probe which is placed adjacent to the outer surface of the test material, for generating an ultrasonic pulse introduced into the test material and for detecting the echoed ultrasonic pulse to measure the transversal time of the echoed ultrasonic pulse, which after determining said measurement of thickness, allows the measurement of the ultrasonic velocity of the test material to be deterimined; and
   c. an eddy current circuit for measuring the relative electrical conductivity of the test material, including an eddy current probe with an eddy current coil which is placed adjacent to the outer surface of the test material and is energized at a relatively high frequency above one megahertz to generate an alternating magnetic field which induces an alternating electric field in the test material having eddy currents and an alternating magnetic field associated therewith, with the associated magnetic field affecting the alternating magnetic field of the eddy current coil, such that the resultant impedence of the eddy current coil in the eddy current circuit provides a measurement of the electrical conductivity of the test material.

2. A composite analyzer tester for nondestructively testing and analyzing the physical properties and gaging the thickness of a test material, as claimed in claim 1, wherein said magnetic induction circuit, said ultrasonic pulse-echo circuit, and said eddy current circuit are implemented in a microprocessor based unit utilizing digital signal processing, and said magnetic induction probe are each attached to and detachable from said unit by electrical plug connections thereto.

3. A composite analyzer tester for nondestructively testing and analyzing the physical properties and gaging the thickness of a test material, as claimed in claim 1, wherein, in using the magnetic induction circuit, an element of uniform magnetic permeability is placed in contact with an inner surface of the test material opposite the placement of the magnetic induction probe on the outer surface thereof to complete a magnetic circuit with the magnetic induction coil, with the test material located therebetween.

4. A composite analyzer tester for nondestructively testing and analyzing the physical properties and gaging the thickness of a test material, as claimed in claim 3, said magnetic induction circuit energizing said magnetic induction coil at a frequency of approximately fifty kilohertz.

5. A composite analyzer tester for nondestructively testing analyzing the physical properties and gaging the thickness of a test material, as claimed in claim 1, said acoustic probe including a piezoelectric transducer which is pulsed to produce an ultrasonic pulse, and which is then monitored for detection of the echoed ultrasonic pulse.

6. A composite analyzer tester for nondestructively testing and analyzing the physical properties and gaging the thickness of a test material, as claimed in claim 5, said ultrasonic pulse circuit energizing said piezoelectric transducer at a frequency of approximately five megahertz.

7. A composite analyzer tester for nondestructively testing and analyzing the physical properties and gaging the thickness of a test material, as claimed in claim 1, said eddy current circuit energizing said eddy current coil at a frequency of approximately five megahertz.

8. A composite analyzer tester for nondestructively testing an analyzing the physical properties and gaging the thickness of a test material, as claimed in claim 1, wherein said magnetic induction circuit is first utilized to measure the thickness of the test material, and said ultrasonic pulse-echo circuit uses the measured thickness in its measurement of the ultrasonic velocity of the test material.

9. A composite analyzer tester for nondestructively testing and analyzing the physical properties and gaging the thickness of a test material, as claimed in claim 1, the test material comprising a graphite-resin composite material.

* * * * *

UNITED STATES PATENT AND TRADEMARK OFFICE
CERTIFICATE OF CORRECTION

PATENT NO. : 4,745,809

DATED : May 24, 1988

INVENTOR(S) : Richard Collins, et al.

It is certified that error appears in the above-identified patent and that said Letters Patent is hereby corrected as shown below:

Column 3, line 13: "eddY" should read as --eddy--

Column 5, line 41, Claim 1: "the material" should read as --the test material--

Column 5, line 43, Claim 1: "of the in the" should read as --of the coil in the--

Column 5, lines 61-62, Claim 1: "deterimed" should read as --determined--

Signed and Sealed this

Twenty-seventh Day of September, 1988

Attest:

DONALD J. QUIGG

Attesting Officer

Commissioner of Patents and Trademarks